(12) United States Patent
Venkatraman et al.

(10) Patent No.: US 9,481,649 B2
(45) Date of Patent: *Nov. 1, 2016

(54) SYNTHESIS OF A NEUROSTIMULATIVE PIPERAZINE

(71) Applicant: NEURALSTEM, INC., Germantown, MD (US)

(72) Inventors: Sripathy Venkatraman, Slingerlands, NY (US); Syed Mahmood, Schenectady, NY (US); Bingidimi I. Mobele, Altamont, NY (US); Olga Lapina, Clifton Park, NY (US); Kellie Vercoe, Guilderland, NY (US); Ying Li, Springfield, NJ (US); Jonathan Salsbury, Madison, WI (US); Mark McLaws, Ballston Lake, NY (US)

(73) Assignee: NEURALSTEM, INC., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/964,397

(22) Filed: Dec. 9, 2015

(65) Prior Publication Data

US 2016/0090358 A1 Mar. 31, 2016

Related U.S. Application Data

(63) Continuation of application No. 13/392,489, filed as application No. PCT/US2010/046537 on Aug. 24, 2010, now Pat. No. 9,278,933.

(60) Provisional application No. 61/236,477, filed on Aug. 24, 2009.

(51) Int. Cl.
*C07D 213/82* (2006.01)
*C07D 213/74* (2006.01)

(52) U.S. Cl.
CPC ........... *C07D 213/74* (2013.01); *C07D 213/82* (2013.01)

(58) Field of Classification Search
None
See application file for complete search history.

(56) References Cited

U.S. PATENT DOCUMENTS

| 7,427,612 | B2 | 9/2008 | Alberati-Giani et al. |
| 7,560,553 | B1 * | 7/2009 | Kelleher-Andersson ... G01N 33/5008 |
| | | | 544/365 |
| 9,278,933 | B2 * | 3/2016 | Venkatraman ....... C07D 213/82 |
| 2006/0040956 | A1 | 2/2006 | Chen et al. |
| 2007/0004750 | A1 | 1/2007 | Lorsbach et al. |
| 2008/0027042 | A1 | 1/2008 | Ohkubo et al. |
| 2009/0005363 | A1 | 1/2009 | Glatthar et al. |

FOREIGN PATENT DOCUMENTS

| CN | 1671700 | 9/2005 |
| WO | WO-03/084942 | 10/2003 |

OTHER PUBLICATIONS

Abdel-Magid et al., "Reductive Amination of Aldehydes and Ketones with Sodium Triacetoxyborohydride. Studies on Direct and Indirect Reductive Amination Procedures," J. Org. Chem. (1996) 61:3849-3862.
International Search Report and Written Opinion for International Application No. PCT/US2010/046537, mailed Oct. 15, 2010, 8 pages.
Notice of the First Office Action for CN 201080046515.5, mailed Mar. 12, 2013.
Search Report and Written Opinion for SG 201201287-8, mailed Jun. 26, 2014, 15 pages.

* cited by examiner

*Primary Examiner* — Emily Bernhardt
(74) *Attorney, Agent, or Firm* — Morrison & Foerster LLP

(57) ABSTRACT

The invention describes an improved synthesis for piperazine derivatized with nicotinic acid and a benzyl moiety. The product compounds are useful for treatment of neurological conditions.

1 Claim, 4 Drawing Sheets

Step 2 process-flow diagram

SYNTHESIS OF A NEUROSTIMULATIVE PIPERAZINE

CROSS-REFERENCE TO RELATED APPLICATIONS

This application is a continuation of U.S. application Ser. No. 13/392,489, having an international filing date of 24 Aug. 2010, which is the national phase of PCT application PCT/US2010/046537 having an international filing date of 24 Aug. 2010, which claims benefit of U.S. patent application No. 61/236,477 filed 24 Aug. 2009. The contents of the above patent applications are incorporated by reference herein in their entirety.

TECHNICAL FIELD

The present invention relates to a synthesis method for compounds and their salts useful as neurogenesis agents. More specifically, the invention is directed to a method to prepare disubstituted piperazines coupled with benzyl and nicotinic acid moieties.

BACKGROUND ART

U.S. Pat. No. 7,560,553, incorporated herein by reference, describes various compounds, including the class of compounds whose synthesis is described herein, as neurogenesis agents. Thus, the compounds prepared according to the invention method are useful in the treatment of various conditions which benefit from promoting neurogenesis by proliferation/differentiation of human hippocampal multipotent stem/progenitor cells and neuronal progenitors. Such conditions include Alzheimer's disease, mild cognitive impairment, dementia, stroke, traumatic brain injury, spinal cord injury, schizophrenia and the like. The synthesis method provided by the invention avoids the use of controlled substances such as benzyl piperazine.

DISCLOSURE OF THE INVENTION

The invention method employs piperazine either protected at one of the ring nitrogens or by selective reaction on only one ring nitrogen, and a substituted nicotinic acid as starting materials and culminates in providing disubstituted piperazine comprising a benzyl substitution at one of the ring nitrogens. The synthesis may further include conversion of this disubstituted piperazine to a suitable salt. Thus, in one aspect, the invention is directed to a method to synthesize a compound of the formula:

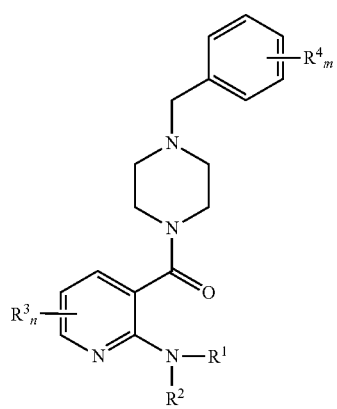

(1)

wherein
$R^1$ is alkyl;
$R^2$ is H or alkyl;
each $R^3$ and $R^4$ is independently alkyl, alkenyl, halo, aryl, heteroaryl, arylalkyl, heteroarylalkyl, $NR_2$, SR, or OR where R is alkyl or aryl;
n is 0, 1 or 2;
m is 0, 1, 2 or 3;
which method comprises reacting a compound of the formula

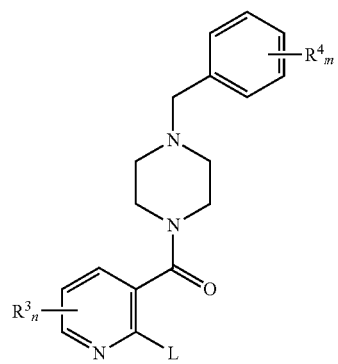

(2)

where $R^3$, $R^4$, m and n are as defined in formula (1) and L is a leaving group,
with a compound of the formula

wherein $R^1$ and $R^2$ are as defined in formula (1).

The compound of formula (2) may be prepared by reacting a compound of formula

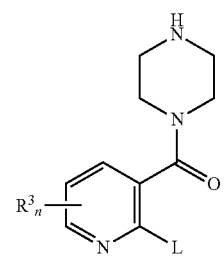

(3)

wherein $R^3$ and n are as defined in formula (1) and L is a leaving group,
with a compound of the formula

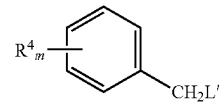

wherein $R^4$ and m are as defined in formula (1), and L' is a leaving group, or with a compound of the formula

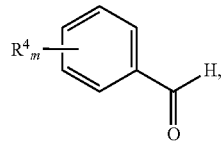

to form an imine followed by reducing said imine

In turn, the compound of formula (3) may be obtained by reacting a compound of the formula

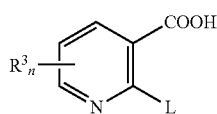

(4)

wherein $R^3$ and n are as defined in formula (1) and L is a leaving group,
with a compound of the formula

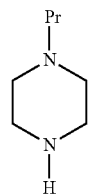

wherein Pr is a protecting group,
followed by removing the protecting group or selectively coupling with one nitrogen using unprotected piperazine. The reaction employing a protecting group may be done either by contracting the compound of formula (4) with the protected piperazine in the presence of a peptide coupling agent or by converting the compound of formula (4) to the corresponding benzoyl halide and adding the protected piperazine in the presence of mild base.

The compound of formula (1) may also be converted to a suitable acid addition salt such as the sulfate, phosphate, hydrohalide, citrate, fumarate, tosylate, or besylate salt. Both mono and bis salts may be formed.

MODES OF CARRYING OUT THE INVENTION

Figure 1:
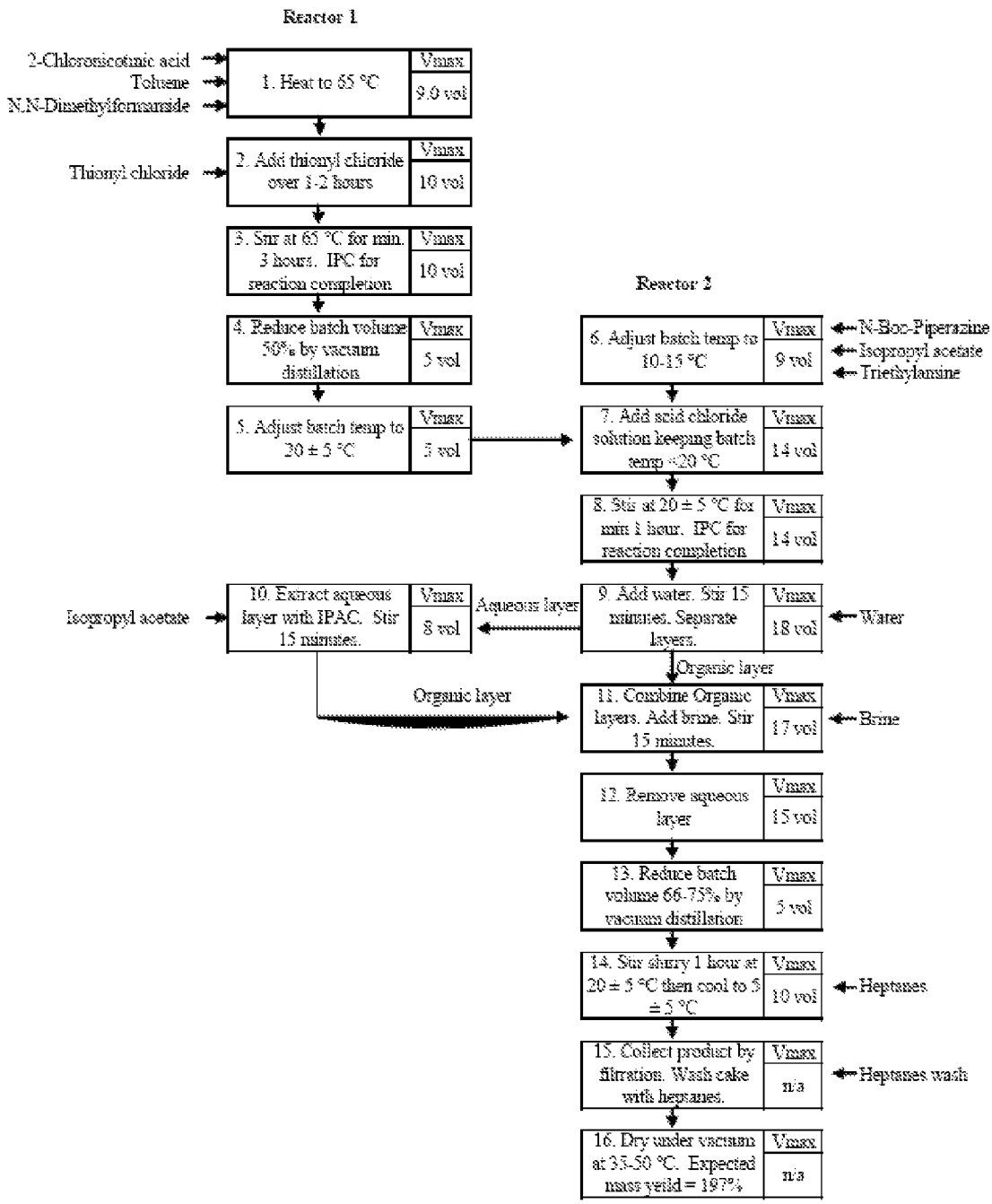
FIG. 1 shows an Optimal Process for Step 1B of Scheme 1.
Figure 2:
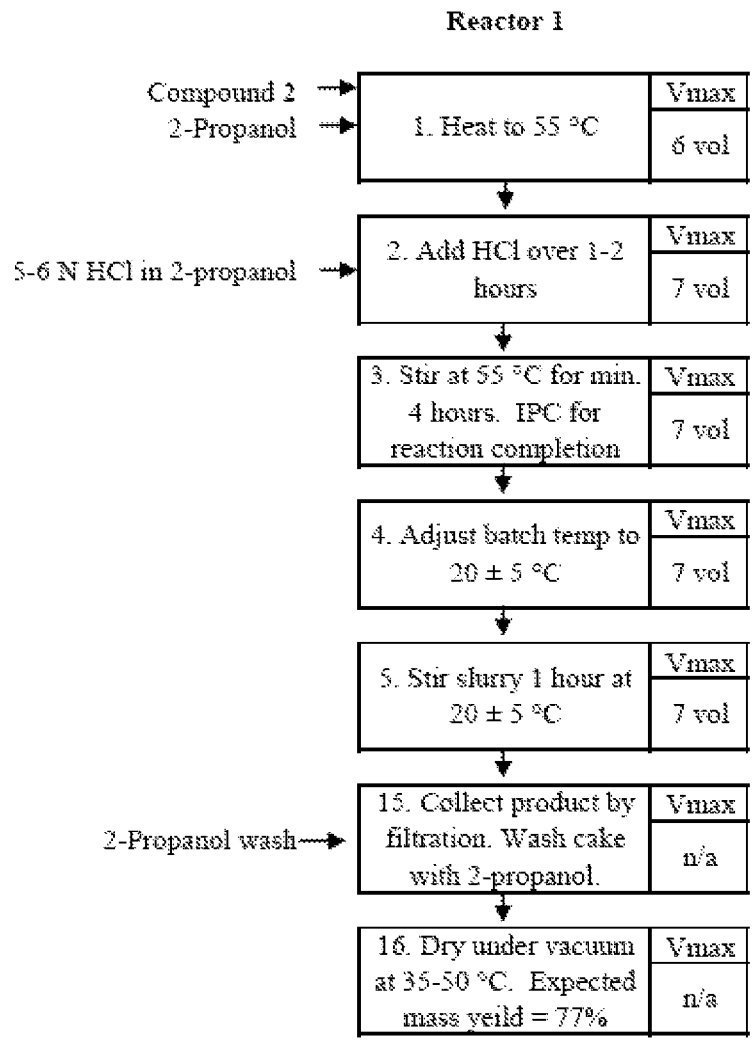
FIG. 2 shows an Optimal Process for Step 2 of Scheme 1.
Figure 3:
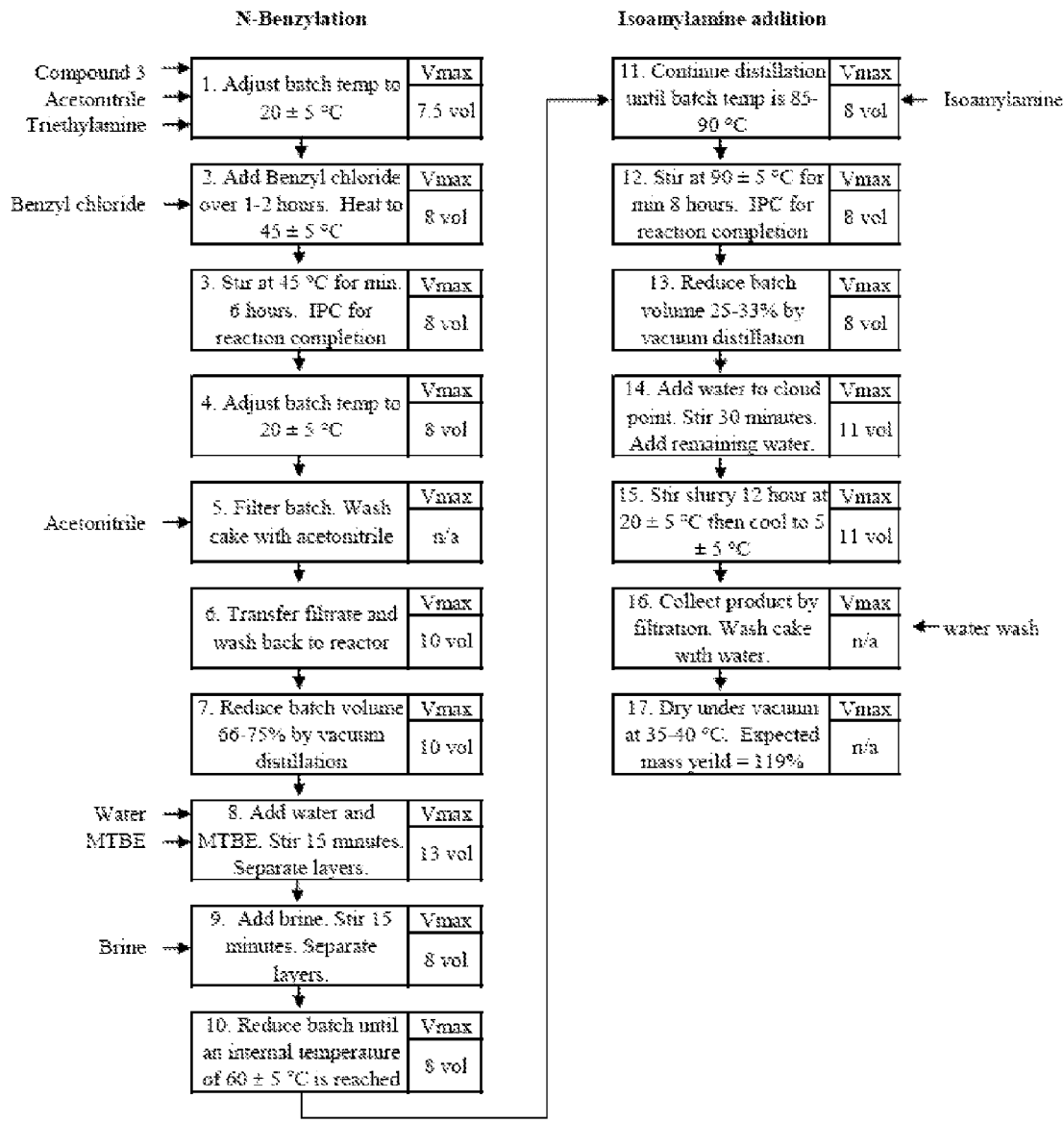
FIG. 3 shows an Optimal Process for Steps 3 and 4 of Scheme 1.
Figure 4:
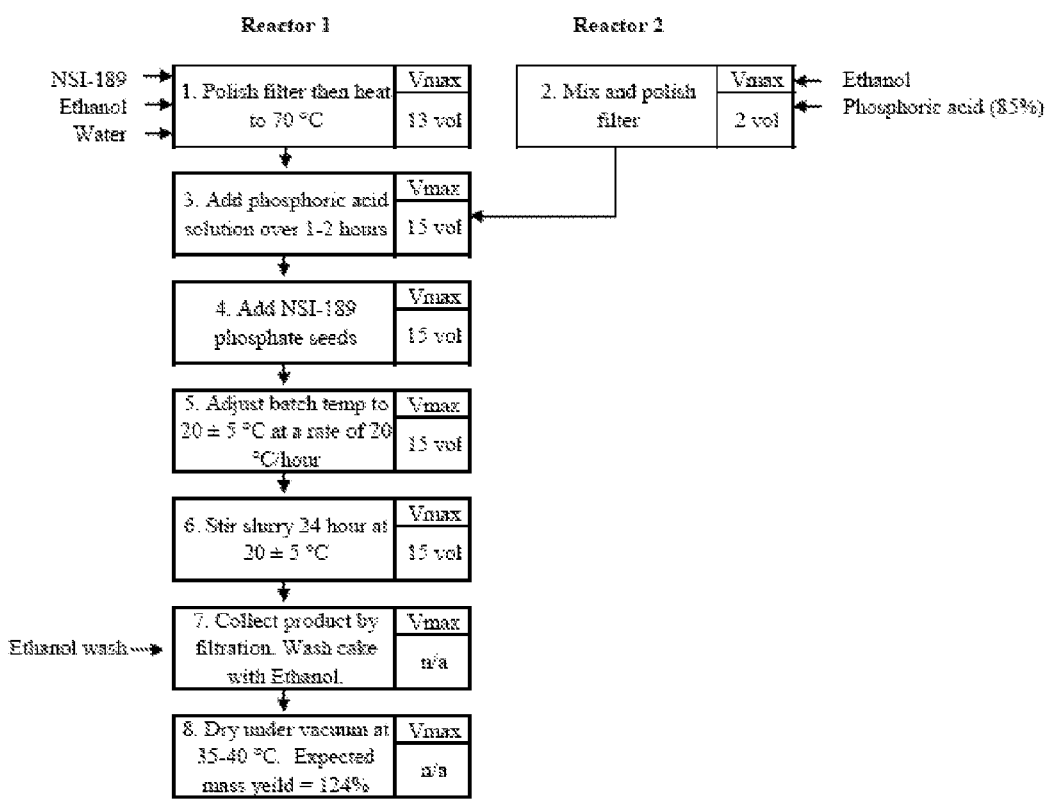
FIG. 4 shows an Optimal Process for Step 5 of Scheme 1.

The compound of formula (1) and its salts, and in particular the compound of formula 1E and its salts have been demonstrated to have neurogenesis activity as described in the above-referenced U.S. Pat. No. 7,560,553. The present invention is directed to an improved method for synthesis of these compounds as illustrated below in Examples 1-5.

More generally, the synthesis of these compounds comprises the following steps.

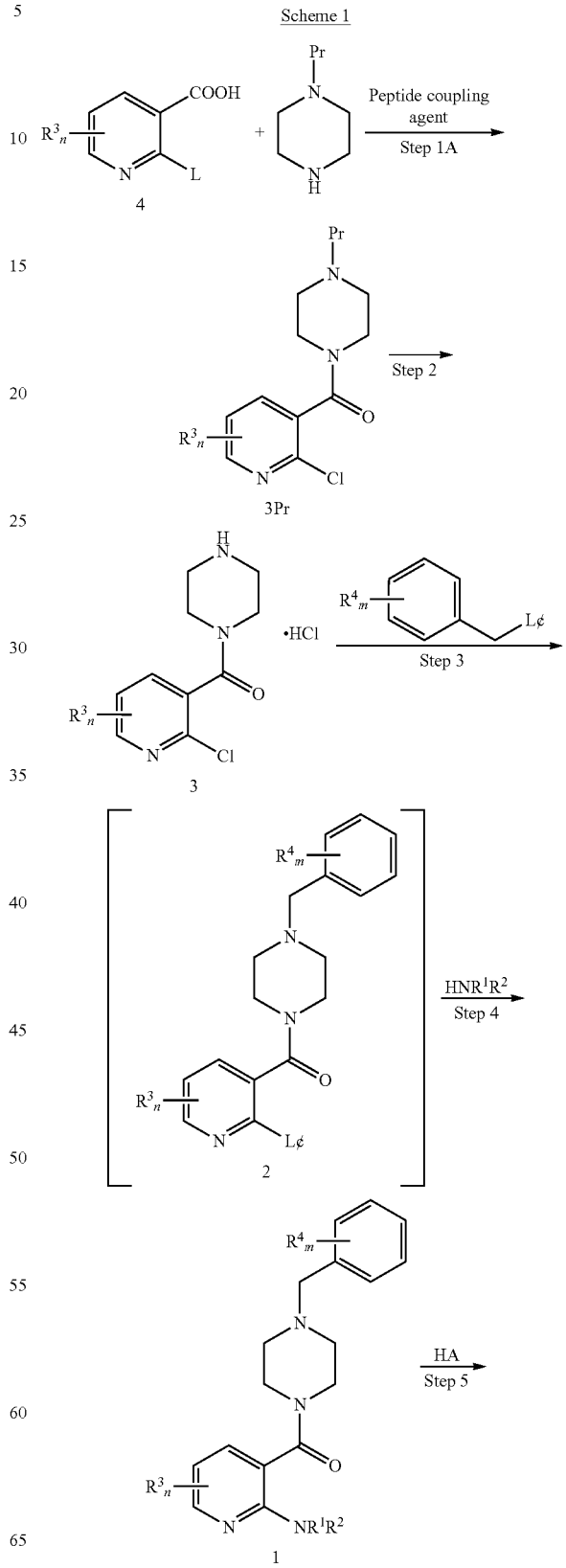

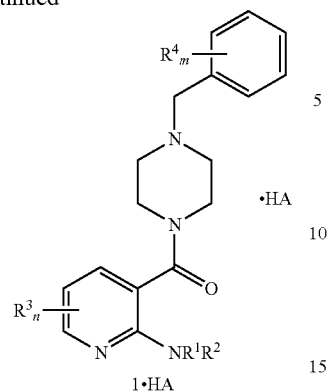

1·HA

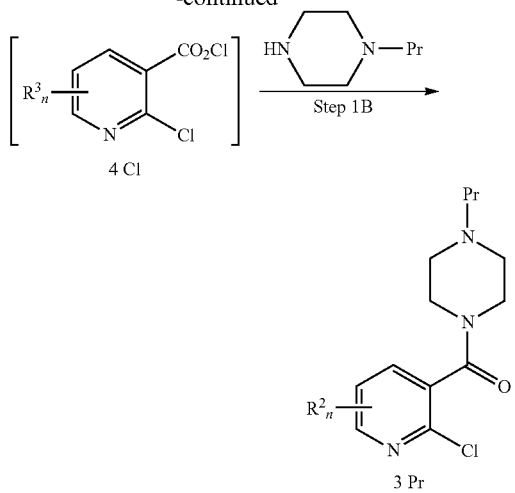

3 Pr

As shown in Scheme 1, optionally substituted nicotinic acid containing a leaving group at position 2 is reacted with semi-protected piperazine in the presence of a peptide coupling agent in the presence of mild base and an appropriate solvent. Typically, the reaction proceeds at ambient conditions to provide a protected form of the compound of formula (3), which is then deprotected in acid in a hydrophilic solvent at slightly elevated temperatures. The resulting product of formula (3) is reacted with optionally substituted benzyl containing a leaving group at the methylene portion in the presence of mild base and suitable solvent, also at elevated temperatures to provide the compound of formula (2) which need not be isolated, but reacted with a primary or secondary amine at elevated temperatures and an appropriate solvent to obtain the compound of formula (1). The compound of formula (1) may then be reacted with 1 or 2 mol of acid to obtain an acid addition salt. If step 3 is conducted by substituting a benzaldehyde for benzyl-L', an imine is formed which is then reduced to the amine using sodium borohydride, sodium cyanoborohydride, sodium triacetoxyborohydride or lithium borohydride in almost any organic solvent.

Typically, the temperature at which step 1A is conducted is between 20° C. and 30° C.; typical bases include triethylamine or other tertiary amines and an excess of a semipolar non-protic solvent such as butyl acetate or isopropyl acetate. Step 2 is typically conducted between 50° C. and 60° C. using strong acid such as HCl or sulfuric acid in the presence of an alcohol solvent. Steps 3 and 4 are conducted between 45° C. and 60° C. for step 3 and between 80° C. and 90° C. for step 4. Step 3 is conducted using a mild base such as triethylamine and an aprotic solvent such as acetonitrile or DMSO. Step 4 is also conducted in the presence of an aprotic solvent.

Step 5 is carried out under conditions dependent on the nature of the acid; either one or two equivalents of the acid may be used to obtain a suitable salt.

In an alternative to step 1A, the compound of formula (3 Pr) may be prepared using step 1B avoiding the use of an expensive peptide coupling agent:

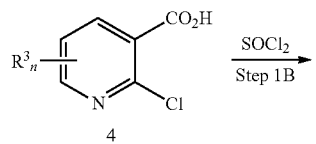

Step 1B is conducted between 60° C. and 70° C. in the presence of a base, such as a tertiary amine, in an excess of a semipolar non-protic solvent such as butyl acetate or isopropyl acetate. Thus, step 1B is conducted under conditions similar to those of step 1A except that the nicotinic acid is converted to the acyl halide in the presence of $SOCl_2$.

The remainder of the scheme may remain the same although the yield may be improved by slightly lowering the temperature at which step 3 is conducted.

As noted above, both $R^1$ and $R^2$ may be alkyl and also alkyl substituents are included among those optionally present on the nicotinic acid and benzyl moieties; further, $NR_2SR$ OR may be substituents where R is alkyl. The substituents $R^3$ and $R^4$ may also be alkenyl.

As used herein, the terms "alkyl," and "alkenyl" include straight-chain, branched-chain and cyclic monovalent hydrocarbyl radicals, and combinations of these, which contain only C and H when they are unsubstituted. Examples include methyl, ethyl, isopropyl, isobutyl, cyclohexyl, cyclopentylethyl, 2-propenyl, 3-butenyl, and the like. The total number of carbon atoms in each such group is sometimes described, e.g., when the group can contain up to 10 carbon atoms it can be represented as 1-10C or as C1-C10 or C1-10. In general, it is preferred that one of $R^1$ and $R^2$ be H and the other alkyl with a maximum of 10 or 8 carbon atoms, and $R^3$ and $R^4$ when embodied as alkyl or alkenyl typically contain a maximum of 8 or 6 carbon atoms.

Typically, the alkyl and alkenyl substituents of the invention contain 1-10C (alkyl) or 2-10C (alkenyl). Preferably they contain 1-8C (alkyl) or 2-8C (alkenyl). Sometimes they contain 1-4C (alkyl) or 2-4C (alkenyl). A single group can include more than one double bond; such groups are included within the definition of the term "alkenyl."

Alkyl and alkenyl groups may be unsubstituted or substituted to the extent that such substitution makes sense chemically from the standpoint of the synthesis procedure and the properties of the end product. Unsubstituted forms are preferred.

As further noted above, $R^3$ and $R^4$ may also be aryl or heteroaryl.

As used herein, "aryl" refers to a monocyclic or fused bicyclic moiety having the characteristics of aromaticity; examples include phenyl and naphthyl. Similarly, "heteroaryl" refers to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, thienyl, furanyl, pyrrolyl, pyrazolyl, thiazolyl, isothiazolyl, oxazolyl, isoxazolyl and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Similarly, "arylalkyl" and "heteroarylalkyl" refer to aromatic and heteroaromatic ring systems which are bonded to their attachment point through a linking group such as an alkylene, including saturated or unsaturated, cyclic or acyclic linkers which optionally contain one or more hetero atoms selected from O and S. Typically the linker is C1-C8 alkyl or a C1-C8 heteroalkyl linker. An arylalkyl group may be, for instance, a phenyl ring and a C1-C4 alkylene where the alkyl or heteroalkyl groups can optionally cyclize to form a ring such as cyclopropane, dioxolane, or oxacyclopentane.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)— and —$C(Me)_2$— may also be referred to as alkylenes, as can a cyclic group such as cyclopropan-1,1-diyl.

Aryl, heteroaryl, arylalkyl and heteroarylalkyl groups maybe unsubstituted or substituted to the extent that such substitution makes sense chemically from the standpoint of the synthesis procedure and the properties of the end product. Unsubstituted forms are preferred.

"Halo", as used herein includes fluoro, chloro, bromo and iodo. Chloro and bromo are often preferred.

Suitable leaving groups for L and L' include halo, such as chloro, IODO or bromo, tosylates (OTs), and triflates OTf). Other suitable leaving groups include mesylates (OMs), and brosylates (OBr).

Peptide coupling agents include O-(benzotriazol-1-yl)-N,N,N',N'-tetramethyluronium tetrafluoroborate (TBTU) as well as 1-ethyl-3-(3-dimethylaminopropyl)-carbodiimide hydrochloride (EDC), N-hydroxybenzotriazole (HOBt), carbonyl diimidazole (CDI), 2-(7-azabenzotriazol-1-yl)-N,N,N',N'-tetramethyluronium hexafluorophosphate (HATU), N,N' Dicyclohexyl carbodiimide (DCC), and N-hydroxy succinamide (NHS).

Suitable protecting agents include 9-fluoroenyl methyl carbamate (Fmoc), and t-butyl carbamate (Boc) as well as TBDMS, TMS, TES, TIPS, TBDPS, benzoyl and carbamates or amides in general.

These lists are non-exhaustive and many suitable leaving groups, protecting groups, and peptide coupling agents are known in the art and many are commercially available.

All these reactions can be done in organic solvents or aqueous organic solvents such as tetrahydrofuran (THF), dimethyl formamide (DMF), methylene chloride, MTBE, all alkanes, NMP, DMA, EtOAc, and in other than for step (2), except for alcoholic solvents).

Preferred embodiments include those wherein $R^2$ is H and $R^1$ is ethyl, propyl, butyl or amyl including the iso forms thereof. Further preferred forms are those wherein m and/or n are 0 or 1, preferably 0. Preferred leaving groups are halo, preferably chloro.

The following examples are offered to illustrate but not to limit the invention.

Examples 1-5 detail the following series of reactions.

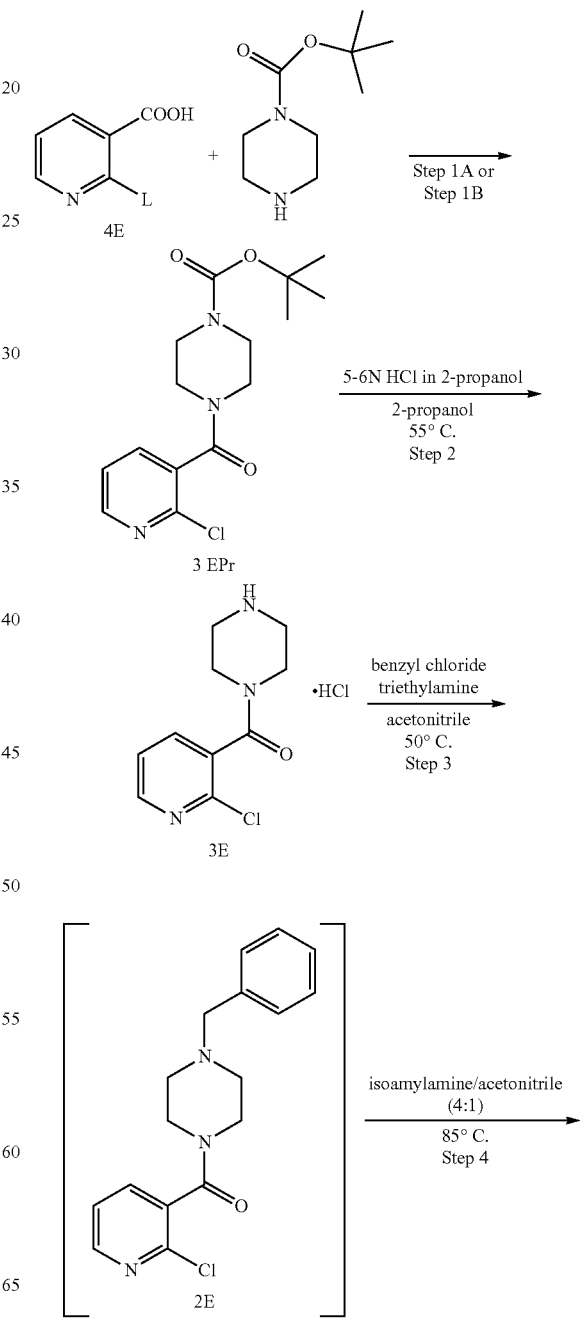

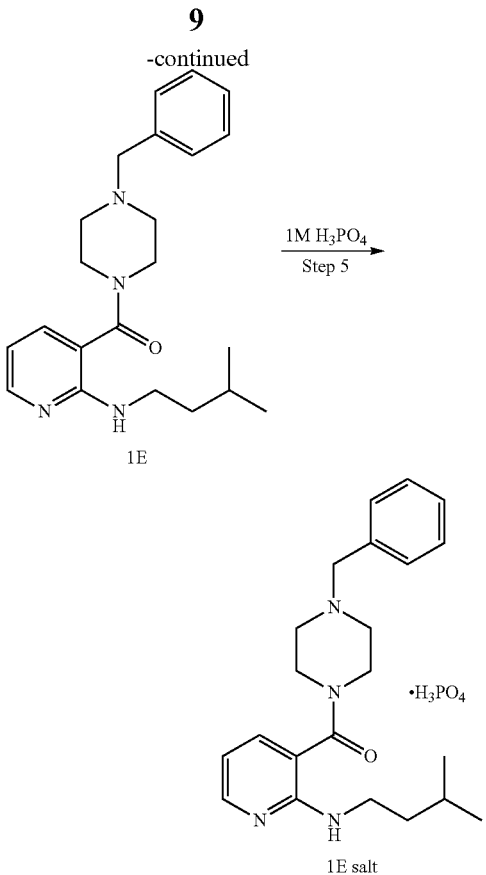

EXAMPLE 1

Preparation of Protected 3E (Step 1A)

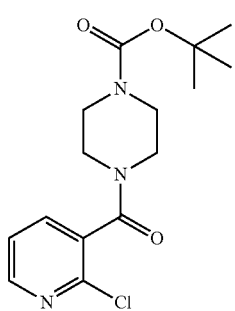

A. Chloronicotinic acid (5.0 g) (4E) was charged to a round-bottom flask followed by acetonitrile (anhydrous, 40 mL) and TBTU (1.4 equiv). To the resulting solution was added triethylamine (2.0 equiv) and the mixture was stirred at ambient temperature for 30 minutes. Boc-piperazine (1.4 equiv) was added in portions keeping the temperature inside the flask at <20° C. The reaction was slowly heated to 40° C. and was judged complete by HPLC analysis after four hours.

The reaction mixture was quenched with a saturated $NaHCO_3$ solution (40 mL) and was extracted with isopropyl acetate (IPAc) (2×40 mL). The organic layers were combined and washed with a 50% brine solution (40 mL). The organic layer was dried over $Na_2SO_4$, filtered and concentrated to one-fourth of the original volume. The resulting oil turned into a thick suspension upon stirring.

Methyl tert butyl ether (MTBE, 100 mL) was added and the resulting suspension was cooled in an ice-water bath and stirred for one hour. The solids were collected by filtration on a Whatman® #1 filter paper and the filter cake was washed with cold MTBE (20 mL). The solid was dried in a vacuum oven at ambient temperature to afford 6.7 g (65% yield) of 3EPr as a light brown solid.

The above reaction was repeated under identical conditions and on the same scale resulting in 6.5 g (65% yield) of 3EPr.

B. The procedure of paragraph A was repeated using 1 g instead of 5 g of chloronicotinic acid and corresponding amounts of other reactants, and using ethyl acetate or isopropyl acetate as solvents. The yields were:

Ethyl acetate: 50% with an HPLC purity of 95.5% (AUC @ 226 nm).

Isopropyl acetate: 80% with an HPLC purity of 97.8% (AUC @ 226 nm).

C. In a modified procedure from paragraph A, chloronicotinic acid (5.0 g) was charged to a round-bottom flask followed by IPAc (reagent grade, 40 mL) and triethylamine (2.0 equiv). To the resulting solution was added TBTU (1.4 equiv) and the mixture was stirred at ambient temperature for 30 minutes. Boc-piperazine (1.4 equiv) was added in portions keeping the temperature inside the flask at <20° C. The reaction was stirred at ambient temperature over the weekend and was judged complete by HPLC analysis after 50 hours. The reaction mixture was quenched with saturated $NaHCO_3$ solution (40 mL) and was extracted with IPAc (2×40 mL). The organic layers were combined and washed with a 50% brine solution (40 mL).

The organic layer was dried over $Na_2SO_4$, filtered and concentrated to one-quarter of the original volume.

To the resulting oil was added MTBE (100 mL) and the resulting suspension was stirred at ambient temperature for 5.5 hours and for another two hours in an ice-water bath. The solids were collected by filtration on a Whatman® #1 filter paper and the filter cake was washed with cold MTBE (20 mL). The product was dried in a vacuum oven at ambient temperature to afford 6.3 g (61% yield) of 4EPr as a light brown solid. The HPLC purity was >99.9% (AUC @ 226 nm).

D. The reaction of paragraph C was scaled up to 10 g and went to completion after 16 hours. The IPAc extract obtained after aqueous workup in the same manner as above was divided in two equal parts. Each part was reduced to 20 g (≈1:1 IPAc/product by weight) under reduced pressure.

Part 1: To the resulting slurry was added MTBE (100 mL). The suspension that resulted was stirred at ambient temperature for 16 hours and for another two hours in an ice-water bath. The solids were collected by filtration on a Whatman® #1 filter paper and the filter cake was washed with cold MTBE (20 mL). The product was dried in a vacuum oven at ambient temperature to afford 6.8 g (66% yield) of 4EPr as a light brown solid. The HPLC purity was >99.9% (AUC @ 226 nm).

Part 2: The process for Part 2 was the same as Part 1 but used heptanes as the antisolvent, resulting in 8.2 g (80% yield) of 4EPr as a light brown solid. The HPLC purity was >99.9% (AUC @ 226 nm).

EXAMPLE 2

Preparation of 3EPr by Step 1B

A. Chloronicotinic acid (5.0 g, 31.7 mmol) was charged to a round-bottom flask followed by toluene (anhydrous, 40 mL) and DMF (120 µL, 0.05 equiv). The resulting slurry was heated to 55° C. and then thionyl chloride (4.6 mL, 2.0 equiv) was added dropwise over five minutes. The slurry was stirred at 55° C. for three hours during which time gas evolution was observed and the mixture turned homogeneous. A sample was taken and quenched into methanol containing triethylamine to give the methyl ester for HPLC analysis. Analysis by HPLC showed the conversion to the acid chloride was complete. The flask was fitted for distillation and heated to reflux. Approximately 20 mL of solvent was removed then the solution was cooled to ambient temperature. A separate flask was charged with N-Boc-piperazine (7.1 g, 1.2 equiv), acetonitrile (30 mL, 6 vol), and triethylamine (13.3 mL, 3.0 equiv). A slight endotherm was noted. The prepared solution of acid chloride was then added at a rate that maintained the internal temperature below 35° C. The resulting slurry was stirred for one hour at ambient temperature. Analysis by HPLC showed the reaction to be complete. The reaction mixture was quenched with saturated NaHCO$_3$ solution (20 mL) and the aqueous layer was extracted with isopropyl acetate (20 mL). The organic layers were combined and washed with water (10 mL). HPLC analysis of the water wash showed some loss of product to the aqueous layer. The organic layer was concentrated to approximately two volumes and then heptanes were added (50 mL) to induce precipitation. The resulting slurry was stirred at ambient temperature for 30 minutes, cooled to 0-5° C. for one hour, filtered, and washed with heptanes. The wet cake was then dried overnight under vacuum to give 9.85 g of 3EPr [MDM-W-1(14), 95% yield, 99.8 area % by HPLC] as a light yellow solid.

B. The procedure of paragraph A of this Example was conducted using 1.2 equivalents of thionyl chloride and 1.1 equivalents of N-Boc-piperazine. The reaction of 2-chloronicotinic acid with thionyl chloride was done at 65° C. to better control gas evolution. The reaction of the acid-chloride intermediate and N-Boc-piperazine was done in IPAc instead of acetonitrile to help prevent precipitation of sodium bicarbonate during the quench. The reaction yielded 3EPr as an off-white solid [MDM-W-5(8), 9.83 g, 95% yield, >99.9 area % by HPLC].

C. The quench and workup of the reaction with aqueous sodium bicarbonate solution can lead to an emulsion that requires time to separate. Switching to a water quench alleviated this problem on a small scale; however as the scale increased, a significant rag layer persisted. The rag layer could be dissolved by slightly warming the biphasic mixture to 30-35° C.

EXAMPLE 3

Deprotection (Step 2)

A. 1-g of 3EPr prepared in Example 1 or Example 2 was treated with 2 equivalents HCl and 5-6N TF 2-propanol at 50° C. The reaction was fond to have gone to completion in 6 hours.

B. The method of paragraph A was repeated with 6.7 g of 3EPr. To a solution of 3EPr (6.65 g) in 2-propanol (5 vol) was added 5-6 N HCl in 2-propanol (2 equiv). The reaction was heated to 40° C. and was judged complete by HPLC analysis after four hours. A white suspension formed during this time.

The reaction was cooled to ambient temperature and the solids were collected by filtration on a Whatman® #1 filter paper. The filter cake was washed with 2-propanol (20 mL). The solid was dried under high vacuum to obtain 4.63 g (86% yield) of 3E.HCl as a white solid. The $^1$H NMR was consistent with the assigned structure and the HPLC purity was >99.9% (AUC @ 226 nm).

C. The process of paragraph A was repeated using 11.5 g of 3EPr. To a solution of 3EPr (11.5 g) in IPA (70 mL, 6 vol) was added 5-6 N HCl in IPA (2 equiv). The reaction was heated to 50° C. and was judged complete by HPLC analysis after nine hours. A white suspension formed during this time.

The reaction was cooled to ambient temperature and the solids were collected by filtration on a Whatman® #1 filter paper. The filter cake was washed with IPA (2×15 mL). The solid was dried under high vacuum to obtain 9.01 g (97% yield) of 3E.HCl as a white solid. The $^1$H NMR was consistent with the assigned structure and the HPLC purity was >99.9% (AUC @ 226 nm).

In each of the foregoing cases, addition of the acid in 2-propanol may be carried out at higher temperatures, e.g., 55° C. or 60° C. This better controls the evolution of gas.

D. Compound 3EPr (9.0 g, 27.6 mmol) was charged to a round-bottom flask followed by 2-propanol (5 vol). The slurry was heated to 55° C. during which time the mixture turned homogeneous and 5-6 N HCl in 2-propanol (2 equiv) was added dropwise. The reaction mixture was stirred at 55° C. for four hours during which time a thick suspension formed. HPLC analysis indicated the reaction was complete. The resulting slurry was cooled to ambient temperature and filtered washing with 2-propanol (2 vol). The wet cake was dried under vacuum at ambient temperature to provide 3E [MDM-W-11(3), 6.9 g, 96% yield, >99.9 area % by HPLC].

E. The reaction in paragraph D was scaled six-fold and assessed by reaction calorimetry (RC1, Mettler-Toledo). A gas-flow meter was configured and calibrated to ensure an accurate measurement of gas evolution. Compound 3EPr (56.6 g, 174 mmol) was suspended in 2-propanol (300 mL) and the slurry was heated to 55° C. during which time the mixture became homogeneous. Hydrochloric acid (1 equiv) in 2-propanol (3.8 M) was added via an addition pump at a linear rate over 30 minutes during which time an off-gas was noted and precipitation began. The reaction was then allowed to stir for 30 minutes before adding hydrochloric acid (1 equiv) at the same rate. The resulting slurry was stirred for four hours at 55° C. The slurry was cooled to ambient temperature and filtered washing with 2-propanol to give 44.0 g of a light-yellow solid after drying over the weekend at ambient temperature under vacuum [MDM-W-56(1), 97% yield, >99.9 area % by HPLC]. A very mild endothermic thermal profile was observed giving an enthalpy of reaction of −57.8 kJ/mol and an adiabatic temperature change of −9.6 K. The rate of gas evolution was mild. Integration of the mass-flow curve indicated 3.9 L of gas evolved during the experiment. The mass-flow curve showed that the rate of gas evolution decelerated almost immediately upon the discontinuation of the HCl addition suggesting that gas evolution was reasonably dose-controlled.

EXAMPLE 4

Conversion to 1E (Steps 3 and 4)

A. A crude sample of 3E prepared in Example 3 was complexed with TFA and reacted with benzaldehyde and the product purified by column chromatography (2-6% methanol/DCM). Fractions containing the product were collected and solvent was removed under reduced pressure to obtain compound 2 G as a thick oil. The $^1$H NMR was consistent with the assigned structure. Since 2E was an oil, 3E was converted to compound 1E in a two-step telescoped method.

B. To a 0.6 g sample of 3E.HCl in 2-propanol was added triethylamine (2 equiv) followed by benzyl chloride (1.2 equiv). The resulting suspension was heated to 50° C. when it turned into a clear solution. The reaction was monitored by HPLC and was judged complete after three hours.

The reaction mixture was cooled to ambient temperature and the solids (TEA.HCl salt) were filtered. To the filtrate was added isoamylamine (10 equiv), and the resulting solution was heated to 75° C. The reaction was monitored by HPLC and was found to have undergone only 36% conversion after 48 hours.

C. The procedure of paragraph B was carried out with 3.5 g of 3E.HCl in acetonitrile (20 mL). The reaction was carried out with 1.0 equivalent of benzyl chloride in the presence of triethylamine (3.0 equiv). The reaction was judged complete by HPLC analysis after stirring at 50° C. for 4.5 hours. The reaction mixture was cooled to ambient temperature and the solids were filtered. The filtrate was pumped to dryness. The residue was dissolved in isoamylamine (20 mL) and was heated to 90° C. The reaction was judged complete by HPLC analysis after 24 hours. The reaction mixture was cooled to ambient temperature and the solvent was reduced to adjust the weight of the residue to 9.5 g. To this was added heptanes (30 mL), resulting in the formation of a light brown suspension. This was stirred at ambient temperature for one hour and for another hour in an ice-water bath. The solids were collected by filtration on a Whatman® #1 filter paper and the filter cake was washed with cold water (2×20 mL). The product was dried in a vacuum oven, resulting in 3.98 g (70% yield) of compound 1E with a HPLC purity of >99.9% (AUC @ 226 nm).

D. Alternatively, to an 8.0 g sample of 3E.HCl in acetonitrile (48 mL, 6 vol) was added triethylamine (2.5 equiv) followed by benzyl chloride (1.05 equiv). The resulting suspension was heated to 50° C. when it turned into a clear solution. The reaction was monitored by HPLC and was judged complete after 3.5 hours (3.3% of unreacted 3E.HCl). The reaction mixture was cooled to ambient temperature and the solids (TEA.HCl salt) were filtered.

The filtrate was evaporated to adjust the weight of the solution to 18 g (≠1:1 acetonitrile/product by weight). To this was added isoamylamine (≈4:1 isoamylamine/acetonitrile, 10 equiv of isoamylamine) and the resulting solution was heated to 85° C. The reaction was judged complete by HPLC analysis after 19 hours (3.0% of unreacted 2E). The reaction mixture was cooled to ambient temperature and the solvent was removed under reduced pressure to adjust weight of the solution to 22 g (1 g of solvent per gram of 1E). On cooling a wet solid was obtained and this was triturated with heptanes (6 g per gram of 1E). The suspension was stirred at ambient temperature for 16 hours and the solids were collected by filtration on a Whatman® #1 filter paper and the filter cake was washed with heptanes (20 mL), followed by water (2×20 mL). The product was dried in a vacuum oven at ambient temperature to afford 7.78 g (69% yield over two steps) of 1E as a light brown solid. HPLC purity was >99.9% (AUC @ 226 nm).

E. Steps 3 and 4 were conducted on a 6 g scale following the procedure set forth above. Compound 3E (6.0 g, 22.9 mmol) was suspended in acetonitrile (30 mL) and triethylamine was added (9.6 mL, 3 equiv) followed by benzyl chloride (2.8 mL, 1.05 equiv). The reaction was heated to 50° C. for 24 hours. HPLC analysis at 20 hours and again at 24 hours indicated no further progression (10.4% of 3E remaining) and the reaction was cooled to ambient temperature and filtered to remove ammonium salts. The solution was then concentrated under vacuum to approximately two volumes to give a concentrated solution of crude 2E (80 area % crude purity). Isoamylamine (26 mL, 10 equiv) was then added and the reaction was heated to reflux (81° C.) for 24 hours. HPLC analysis at 20 hours and again at 24 hours indicated no further progression (73 area % crude purity) and the reaction cooled to ambient temperature and was concentrated under reduced pressure to approximately 4 volumes. Heptane (35 mL) was then added and the resulting slurry stirred over the weekend. The thin slurry was filtered and washed with water at which point the solids dissolved leaving nothing on the filter funnel. The biphasic filtrate was extracted with IPAc and then concentrated to an oil. The oil was dissolved in IPA (30 mL); water (36 mL) was slowly added until the solution turned slightly opaque and then a small amount of Compound 1E [DSJ-F-20(15)] was added to induce crystallization. The resulting slurry was filtered washing with water and was dried overnight under vacuum giving 5.46 g of Compound 1E [MDM-W-26(8), 65% yield, 99.9 area % by HPLC, 98.6 wt % by $_1$H NMR].

F. N-Benzylation was evaluated at temperatures ranging from 25° C. to 75° C. to determine the optimal temperature for the reaction and its thermal tolerance. The reaction rate increased with temperature, but all approached a common endpoint of 95-96% conversion after 20 hours regardless of temperature. Analysis by HPLC showed little difference in crude purity, but a notable color change occurred above 45° C. rendering the reaction solution as light orange. A reaction temperature of 45° C. was considered optimum in terms of reaction rate and diminished color change and precipitate shelling.

G. The process was amended by increasing the amount of benzyl chloride to 1.1-1.15 equivalents and by slightly lowering the reaction temperature to 45° C. to reduce discoloration. An aqueous workup after the N-benzylation was incorporated to remove impurities generated during the N-benzylation reaction prior to formation of 1E. Isolation of the product was done by direct crystallization from the reaction mixture (isoamylamine) by adding water as an antisolvent. Loss of product to the filtrate was typically less than 7%. 1E was isolated as a white solid in approximately 80% yield at very high purity.

EXAMPLE 5

Complete Performance of Scheme 1

A. A 50 g sample of 2-chloronicotinic acid was treated with N-Boc piperazine (1.2 equiv) in the presence of triethylamine (2 equiv) and TBTU (1.4 equiv). The reaction was carried out in IPAc (300 mL, 6 vol) and at ambient temperature. The reaction was judged complete by HPLC analysis after 12 hours. After filtration and aqueous workup, the IPAc extract was reduced to 180 g under vacuum (≈1:1 IPAc/product by weight).

To the resulting slurry was added heptanes (≈1:1 IPAc/product by weight). The suspension that resulted was stirred at ambient temperature for 16 hours and for another two hours in an ice-water bath. The product was collected by filtration on a Whatman® #1 filter paper and the filter cake was washed with heptanes (2×25 mL). The product was dried in a vacuum oven at ambient temperature to obtain 78.53 g (76% yield) of compound 3EPr as a brown solid. HPLC purity was 98.9% (AUC @ 226 nm).

B. 73.53 g of compound 3EPr obtained in paragraph A was subjected to the Boc-deprotection reaction in the presence of 2 equivalents of 5-6 N HCl in IPA. The reaction was carried out at 50° C. in IPA (6 vol). The reaction was judged complete by HPLC analysis after seven hours. The reaction mixture was cooled to ambient temperature and was filtered through a Whatman® #1 filter paper. The filter cake was washed with IPA (2×50 mL) and dried under high vacuum to obtain 56.31 g (95% yield) of 3E.HCl as a brown solid. HPLC purity was >99.9%.

C. A sample of 54.0 g of 3E.HCl was then treated with benzyl chloride (1.05 equiv) in the presence of triethylamine (3 equiv). The reaction was carried out at 50° C. in acetonitrile (6 vol). The reaction was judged complete by HPLC analysis after eight hours. The reaction mixture was cooled to ambient temperature and the solids were filtered on a Whatman® #1 filter paper. The filter cake was washed with acetonitrile (2×25 mL). The solvent was removed under reduced pressure to adjust the weight of the solution to 110 g (≈1:1 acetonitrile/product by weight).

To this was added isoamylamine (220 g) to make 4:1 isoamylamine/acetonitrile. The resulting solution was heated to 85° C. and the reaction was judged complete by HPLC analysis after 22 hours. The reaction mixture was cooled to ambient temperature and the solvent was removed under reduced pressure to adjust the weight of the solution to 150 g. To the resulting mixture was added heptanes (6 vol). The suspension was stirred at ambient temperature for 16 hours and the solids were collected by filtration on a Whatman® #1 filter paper and the filter cake was washed with heptanes (250 mL×2), followed by water (250 mL×2). The product was dried in a vacuum oven at ambient temperature to afford 60.66 g (80% yield over two steps) of 1E as a light brown solid. HPLC purity was >99.9% (AUC @ 226 nm).

EXAMPLE 6

Preparation of Phosphate Salt

A. A 22 L, three-neck, round-bottom flask equipped with an addition funnel, a reflux condenser, a thermocouple, and an overhead stirrer was placed in a heating mantle. The flask was charged with ethanol (7.9 L, Pharmco lot #0802062) followed by deionized water (420 mL). Next 1E (700 g, 2.1 mol) was charged to the reactor and the resulting mixture was heated to 75° C. A 1 M solution of $H_3PO_4$ in ethanol (4.5 L, 4.5 mol, 2.1 equiv) was charged as a quick stream over a period of 30 min. The resulting mixture was stirred for 15 min and 1E.$H_3PO_4$ (0.5 g) was added as seed for recrystallization. The resulting clear solution was cooled to ambient temperature at a rate of 20° C./h.

The cooled suspension was allowed to stir at ambient temperature for 11 h and filtered through a Whatman® #1 filter paper. Ethanol (2.8 L×2) was used to aid in the transfer and also to wash the filter cake. The product was dried under vacuum to a constant weight at 25° C. to obtain 1E.$H_3PO_4$ as a white solid (751 g, 62% yield). Analysis by HPLC indicated a purity of >99.9% (AUC @ 226 nm) and $^1$H NMR was consistent with the assigned structure.

B. Compound 1E (4.9 g, 13.3 mmol) was dissolved in a 5% mixture of water in ethanol at 75° C. and then 1 M phosphoric acid in ethanol (2.1 equiv) was added. The resulting solution was cooled to ambient temperature at a rate of 20° C./h during which time a sticky precipitate formed. The mixture was reheated to dissolve the precipitate, and then the system was seeded with 1E phosphate and cooled as described above. The resulting slurry was stirred overnight at ambient temperature and then filtered, washing with ethanol to give 4.9 g of 1E phosphate (79% yield, >99.9 area % by HPLC) as a white solid. The results indicated that seeding was essential to establishing the proper crystal form.

C. Four phosphate salt-formation reactions were conducted on a 10 g scale under the following conditions:

MDM-W-126: 1.25 equivalents $H_3PO_4$, 12 volumes EtOH

MDM-W-128: 1.25 equivalents $H_3PO_4$, 12 volumes 5% water in EtOH

MDM-W-130: 1.0 equivalent $H_3PO_4$, 12 volumes EtOH

MDM-W-131: 1.0 equivalent $H_3PO_4$, 12 volumes 5% water in EtOH

Each reaction was heated to 70° C., seeded with 1E phosphate [0.1 wt %, DAJ-F-40(2)], and cooled to 20° C. at a rate of 20° C./hour. The resulting thick slurry was stirred overnight, filtered (washing with EtOH), and dried to a constant weight. The results of these reactions are shown in Table 1. In general, the slurry obtained from reactions using 5% water in EtOH was more manageable.

TABLE 1

Phosphate Salt Formation Screen

| Reaction | % Yield | Purity (Area %) | Potency (wt %)* |
|---|---|---|---|
| MDM-W-126 | 97 | >99.9 | 105 |
| MDM-W-128 | 95 | >99.9 | 105 |
| MDM-W-130 | 96 | >99.9 | 102 |
| MMD-W-131 | 94 | >99.9 | 103 |

*Potency relative to NCSS batch DAJ-F-40(2).

Physical Properties of the Mono-Phosphate Salt

Solubility in water was >36 mg/mL under ambient conditions, and the salt was crystalline by XRPD analysis.

DSC analysis showed one endothermic event at 179° C. which is consistent with a melt.

Moisture sorption analysis showed the material was moderately hygroscopic, adsorbing 4.4 wt % water at 60% RH and 11.2 wt % at 90% RH.

IC analysis showed a formula (1) to counter-ion ratio of 1:1.6 to 1:2.3 in different batches of the salt.

The invention claimed is:
1. A method to convert a compound of formula (1):

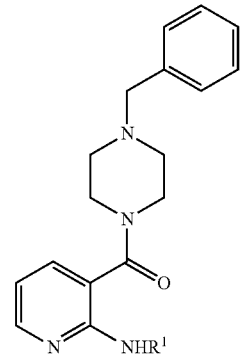

(1)

wherein $R^1$ is isoamyl to a phosphate salt by reacting said compound with phosphoric acid wherein the reaction occurs in a solvent mixture consisting of ethanol and water.

* * * * *